US006418383B1

United States Patent
Wang

(10) Patent No.: US 6,418,383 B1
(45) Date of Patent: Jul. 9, 2002

(54) METHOD AND APPARATUS FOR ITERATIVE SPECTRAL COMPENSATION

(75) Inventor: Yongdong Wang, Wilton, CT (US)

(73) Assignee: PerkinElmer Instruments LLC ( * ) Notice: Subject to any disclaimer, the term of this patent is extended or adjusted under 35 U.S.C. 154(b) by 0 days.

(21) Appl. No.: 09/503,092

(22) Filed: Feb. 11, 2000

(51) Int. Cl.[7] .............................................. G06F 15/82
(52) U.S. Cl. .......................... 702/22; 702/194; 702/76; 702/22
(58) Field of Search .......................... 250/339.01, 328; 364/571.01; 422/68.1; 435/5, 6; 536/22.1; 356/45, 346; 128/660; 702/22

(56) References Cited

U.S. PATENT DOCUMENTS

| | | | | |
|---|---|---|---|---|
| 4,029,401 A | * | 6/1977 | Nather | 250/328 |
| 4,418,281 A | * | 11/1983 | Horrocks | 250/328 |
| 4,427,887 A | * | 1/1984 | Berthold | 250/328 |
| 4,723,553 A | * | 2/1988 | Miwa et al. | 128/660 |
| 5,303,165 A | * | 4/1994 | Ganz et al. | 364/571.01 |
| 5,308,982 A | * | 5/1994 | Ivaldi et al. | 250/339.01 |
| 5,538,848 A | * | 7/1996 | Livak et al. | 435/5 |
| 5,720,923 A | * | 2/1998 | Haff et al. | 422/68.1 |
| 5,723,591 A | * | 3/1998 | Livak et al. | 536/22.1 |
| 5,876,930 A | * | 3/1999 | Livak et al. | 435/6 |
| 5,959,730 A | * | 9/1999 | Wang et al. | 356/346 |
| 6,029,115 A | * | 2/2000 | Tracy et al. | 702/22 |
| 6,057,912 A | * | 5/2000 | Celentano et al. | 356/45 |

FOREIGN PATENT DOCUMENTS

| | | | | |
|---|---|---|---|---|
| GB | 1226834 | * | 3/1971 | |
| WO | 97/46963 | * | 12/1997 | G06F/19/00 |

OTHER PUBLICATIONS

US 5,962,233, 10/1999, Livak et al. (withdrawn)*
Abraham Savitzky and Marcel J. E. Golay, "Smoothing and Differentiation of Data by Simplified Least Squares Procedures", vol. 36, No. 8, Jul. 1964, pp. 1627–1639, Analytical Chemistry.*
Chris Webb et al., "A Fast Automated Spectral Curve–Fitting Technique for ICP–AES", May 1999, pp. 58–63, Spectroscopy.*

* cited by examiner

Primary Examiner—Kamini Shah
Assistant Examiner—Douglas N Washburn
(74) Attorney, Agent, or Firm—St. Onge Steward Johnston & Reens LLC

(57) ABSTRACT

An iterative method and apparatus for correction and compensation of analytical signals, such as spectrometric data, is provided which corrects for spectral cross-talk; compensates for spectral shift; and reduces error propagation. The method and apparatus can be applied to a multicomponent sample analysis using least squares procedure with differentiation while reducing noise propagation.

24 Claims, 5 Drawing Sheets

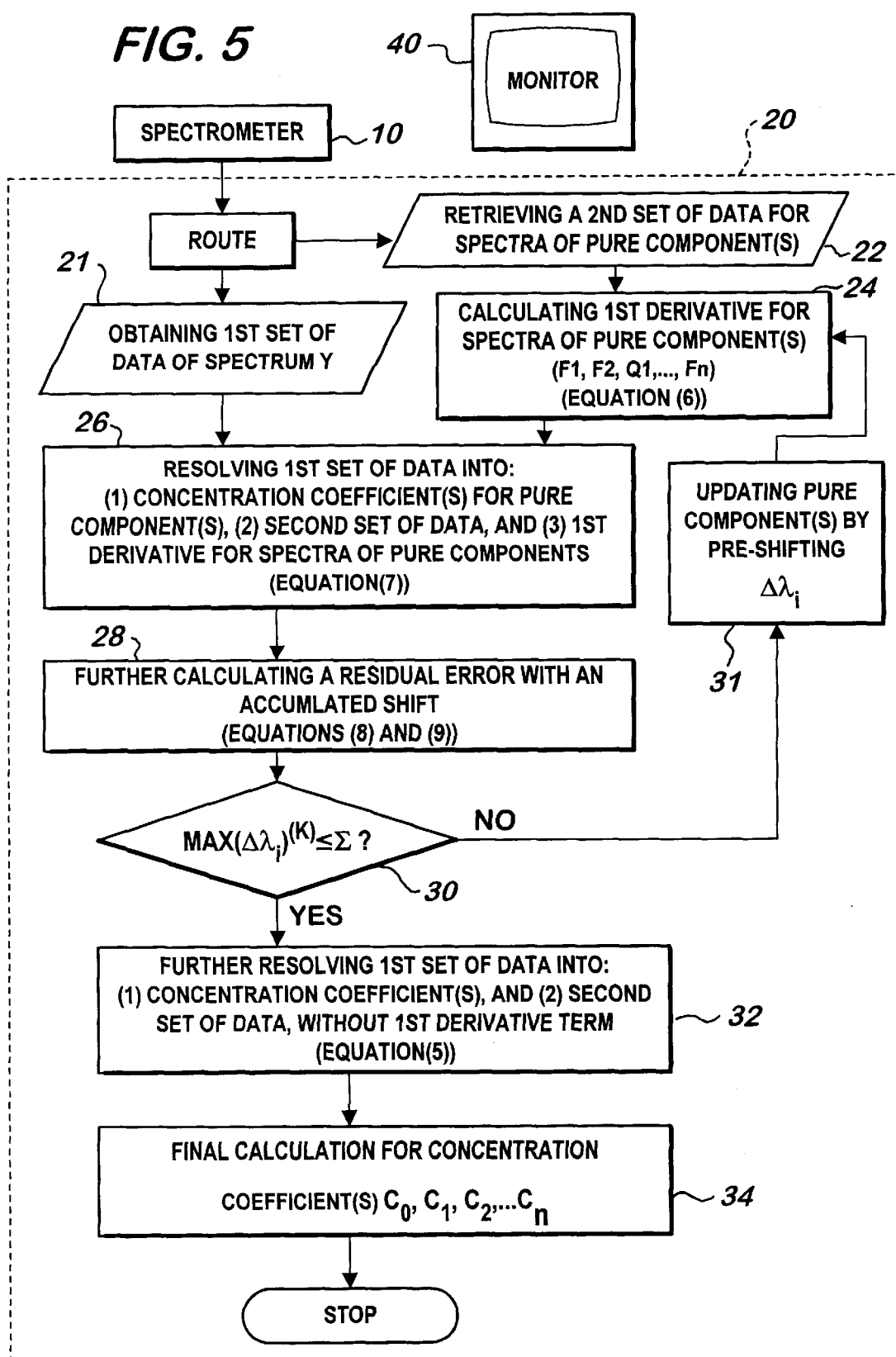

US 6,418,383 B1

METHOD AND APPARATUS FOR ITERATIVE SPECTRAL COMPENSATION

FIELD OF THE INVENTION

The invention relates to a method to compensate for spectral shift associated with spectrophotometric measurements, more particularly to an iterative method using least squares procedure with differentiation for a multicomponent analysis that reduces noise propagation.

BACKGROUND OF THE INVENTION

It is often desired to isolate and determine the presence and/or concentration of a particular element or species contained in a sample. For example, in the field of biotechnology, nucleic acid sequence analysis is becoming increasingly important in many research, medical, and industrial fields, e.g. Caskey, *Science* 236: 1223–1228 (1987); Landegren et al, *Science,* 242: 229–237 (1988); and Arnheim et al, *Ann. Rev. Biochem.,* 61: 131–156 (1992). The development of several nucleic acid amplification schemes has played a critical role in this trend, e.g. polymerase chain reaction (PCR), Innis et al, editors, *PCR Protocols* (Academic Press, New York, 1990); McPherson et al, editors, *PCR: A Practical Approach* (IRL Press, Oxford, 1991); ligation-based amplification techniques, Barany, *PCR Methods and Applications* 1: 5–16 (1991); and the like.

PCR in particular has become a research tool of major importance with applications in cloning, analysis of genetic expression, DNA sequencing, genetic mapping, and drug discovery, e.g. Arnheim et al (cited above); Gilliland et al, *Proc. Natl. Acad. Sci.,* 87: 2725–2729 (1990); Bevan et al, *PCR Methods and Applications,* 1: 222–228 (1992); Green et al, *PCR Methods and Applications,* 1: 77–90 (1991); Blackwell et al, *Science,* 250: 1104–1110 (1990).

Fluorescence-based approaches to provide real time measurements of amplification products during a PCR have been used. See Holland et al, *Proc. Natl. Acad. Sci.,* 88: 7276–7280 (1991). Such approaches have either employed intercalating dyes (such as ethidium bromide) to indicate the amount of double stranded DNA present, or they have employed probes containing fluorescent-quencher pairs (the so-called "Taq-Man" approach) that are cleaved during amplification to release a fluorescent product whose concentration is proportional to the amount of double stranded DNA present.

Spectrometric analysis for quantification of a component in a multicomponent system can be accomplished by measurement at multiple wavelengths such as in inductively coupled plasma optical emission spectroscopy (OES). One of the major problems in handling spectral data of this type arises from overlapped responses from various chemical species in a mixture. See U.S. Pat. No. 5,308,982 to Ivaldi et al., incorporated herein by reference. In the case of PCR analysis, as more targets are sought to be identified in a multicomponent analysis, more fluorescent dyes are used simultaneously. The spectral peaks of different fluorescent dyes tend to overlap to varying degrees to begin with, and as more dyes are used simultaneously, their respective peaks necessarily become closer together in terms of wavelength. As such peaks become closer together, the likelihood of component "cross-talk" (i.e, the correlation among estimated concentrations of various components) resulting from an improper component fit increases correspondingly.

Another problem arises from a phenomenon known as "spectral shift" where the measured wavelength of the component shifts. Such shifts cause the peaks of components in the sample to appear to be at different wavelengths than the previously recorded peaks of the pure components. Such apparent shifts may occur, for example, between instruments and even, with time, in the same instrument. In the case of PCR analysis, such spectral shift can be caused by a number factors related to the chemistry of the reaction (i.e. pH change), as well as the instrument hardware. When spectral shift occurs in a PCR analysis, the "pure dye" or pure component signals are shifted slightly in terms of wavelength (i.e., they peak at a slightly different frequency) as compared to their appearance when measured individually or at the start of the reaction. Such a phenomenon has a detrimental effect on the accuracy of DNA sequence analysis and quantification since spectral shift can alter the degree of overlap among dye peaks, thereby increasing the likelihood of component cross-talk.

In dealing with the problem of spectral shift generally, the prior art approach has been to use interpolation. The spectral information is collected at discrete points. If a wavelength shift is required, it is necessary to know what the data is between such points. However, since the amount of interpolation is not known, it is required to successively check the error and iterate. This also is a mathematically and time intensive procedure.

U.S. Pat. No. 5,023,804 (Hoult) discloses comparing spectral data with a standard spectrum by computing a normalized dot product of a sample spectrum and the standard spectrum. The two spectra are weighted by filtering to remove short and long periodicities, the filtering being effected with a triangular wave using a simplified algorithm.

U.S. Pat. No. 4,997,280 (Norris) discloses a spectrophotometric instrument in which rapid scanning causes distortion of the spectrum. A first derivative is determined from the spectrum and multiplied by a constant selected to correct for the distortion. The resulting product values are added to the distorted spectrum to provide a set of corrected values for intensity. The selected constant is determined by comparing data acquired from operation of the instrument at a normally rapid speed and then slowly, in order to eliminate the distortion.

Another prior art method uses the Kalman filter, as disclosed in an article "Some Spectral Interference Studies Using Kalman Filtering in Inductively Coupled Plasma-Atomic Emission Spectroscopy" by E. H. van Veen, F. J. Oukes and M. T. C. de Loos-Vollebregt, *Spectrochimica Acta 45B,* 1109–1120 (1990). This is an iterative process. A set of coefficients is estimated. These coefficients are employed to multiply each data point in the spectrum. The error between the results and each data point is computed. A derivative is then estimated that indicates the direction in which to shift the estimates of the coefficients. Accordingly, there is a successive refinement of the error which, after many iterations, converges.

U.S. Pat. No. 5,308,982 (Ivaldi et al.) discloses a method which incorporates a derivative of sample spectral data into a matrix model to compensate for spectral shift. This is a standardization that requires spectral data to be acquired in relatively small spectral increments to achieve sufficient representation of the derivative in the model. Wavelength increments of spectral data ordinarily are limited by pixel size of the detector. Smaller increments are achieved by slit scanning in which the inlet slit to the spectrometer is imaged on a pixel. Varying the lateral position of the slit in small steps effectively moves a spectrum across the pixels to obtain spectral data in smaller increments. Although utilized for collecting archive data, it is preferable that slit scanning be avoided to speed up ordinary data acquisition.

One of the problems with the aforementioned methods is that they are computational and time intensive, requiring many iterations. This becomes a particular problem in the case of real time quantification with spectra collected at 96 Hz or more.

Another problem with the prior methods for spectral compensation, such as those including differentiation, is the propagation of noise. For example, a first derivative for each pure component signal in a multicomponent matrix can be calculated to improve the fit for the spectral shift. While this approach has worked reasonably well, it unfortunately adds a considerable amount of noise to the calculated pure components due to the increased spectral overlaps among the increased number of components and their derivatives.

What is desired, therefore, is a method and apparatus to detect the concentrations of species in a multicomponent mixture which is less computational and time intensive, corrects for spectral shift and reduces the propagation of noise in the computation.

SUMMARY OF THE INVENTION

Accordingly, an object of the invention is to provide a method for the analysis of spectral signals for a multicomponent mixture in order to calculate the quantities of the individual components.

Another object of the invention is to provide a method which resolves overlapping spectral responses of a mixture containing a plurality of spectrally independent species.

A further object of the invention to provide a method applying a linear regression technique in which pure component signals are fit to raw measured spectral data of a multicomponent system using a least squares approach.

Yet another object of the invention is to provide a method which corrects for spectral shift in a spectral analysis that is less computational and time intensive.

Another object of the invention is to provide a spectrometric method to calculate the quantities of individual components in a multicomponent mixture which reduces the propagation of noise.

To overcome some of the disadvantages of the prior art and achieve at least some of the objects and advantages listed above, the present invention comprises: a method for compensating for spectral shift in the spectrometric analysis of a sample; and in another aspect, a method for resolving a signal into at least one separate component and compensating for a signal shift in the analysis of a sample, and in a further aspect, an apparatus for compensating for spectral shift in the spectrometric analysis of a sample.

A method according to the invention for compensating for spectral shift in the spectrometric analysis of a sample comprises steps of: obtaining a first set of data corresponding to a spectrum of the sample; retrieving a second set of data corresponding to spectra for at least one pure component of the spectrum; calculating a first derivative for the second set of data; resolving the first set of data into the second set of data, the first derivative, and at least one concentration co-efficient for the pure component; pre-shifting the second set of data to compensate for the spectral shift; further calculating a residual error associated with the spectral shift for the first set of data; comparing the residual error with a pre-determined value; and repeating the pre-shifting, further calculating and comparing steps until the residual error is within the pre-determined value.

The invention in one of its aspects also provides a method for resolving a signal into at least one separate component and compensating for a signal shift in the analysis of a sample comprising steps of: resolving the signal into a first set of data of at least one separate component and a second set of data of at least one coefficient for the separate component; retrieving the first set of data corresponding to the component of the sample; calculating a first derivative for the first set of data; second resolving the signal into the first set of data, the second set of data, and the first derivative; pre-shifting the first set of data to compensate for the signal shift; further calculating a residual error associated with the signal shift for the signal; and comparing the residual error with a pre-determined value; and repeating the pre-shifting, further calculating and comparing steps until the residual error is within the pre-determined value.

In another aspect, the invention provides an apparatus for compensating for spectral shift in the spectrometric analysis of a sample comprising: a device for obtaining a spectrum of the sample; a computer linked to the device; software executing on the computer for obtaining a first set of data corresponding to the spectrum of the sample; software executing on the computer for retrieving a second set of data corresponding to spectra for at least one pure component of the spectrum; software executing on the computer for calculating a first derivative for the second set of data; software executing on the computer for resolving the first set of data into the second set of data, the first derivative, and at least one concentration coefficient for the pure component; software executing on the computer for pre-shifting the second set of data to compensate for the spectral shift; software executing on the computer for further calculating a residual error associated with the spectral shift for the first set of data; software executing on the computer for comparing the residual error with a pre-determined value; and software executing on the computer for repeating the pre-shifting, further calculating and comparing steps until the residual error is within the pre-determined value.

In another aspect of the invention, the method and apparatus comprise the step of further resolving the first set of data into the second set of data and at least one concentration coefficient for the pure component without use of the first derivative.

The invention and its particular features will become more apparent from the following detailed description with reference to the accompanying drawings.

BRIEF DESCRIPTION OF THE DRAWINGS

FIG. 5 is a logic flow diagram using the iterative spectral compensation method of the present invention.

DETAILED DESCRIPTION OF THE INVENTION

The method of the present invention involves correction and compensation of spectrometric data or move generally, signals, in three aspects, namely (1) correction for spectral "cross-talk"; (2) compensation for spectral shift; and (3) minimization of error propagation.

Figure 1:
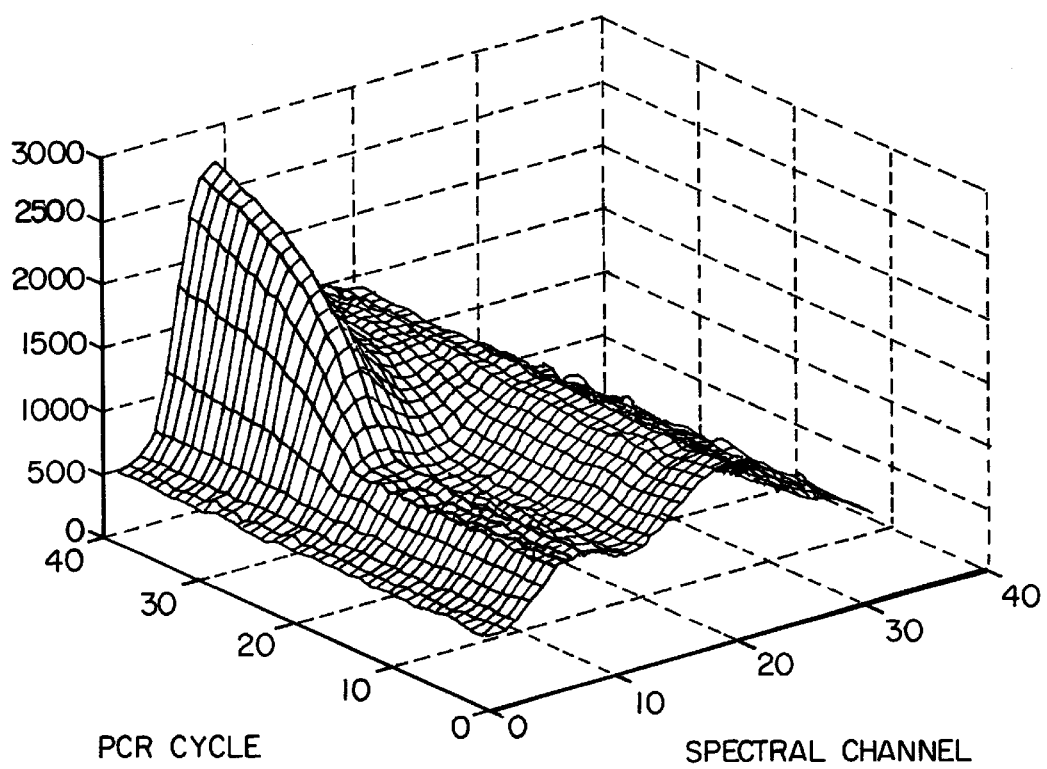
FIG. 1 shows the fluorescence spectra in three dimensions typically observed as result of measuring amplification products during a PCR reaction.

In one application of the invention, as an example and not as a limitation to the present invention, in the case of PCR analysis, the raw spectral data, illustrated in FIG. 1, measured by a spectrophotometer from a PCR instrument such as 7700 Sequence Detection System (SDS 7700) manufactured by PE Applied Bio-Systems, Foster City, Calif. may be represented by a multicomponent model which may be written in equation form as:

$$Y(\lambda) = C_0[BKGD] + C_1[F_1] + C_2[F_2] + C_3[Q] + \ldots + C_n[Fn] + e \quad (1)$$

where $Y(\lambda)$ represents a first set of data corresponding to a spectrum of the sample.

$C_0$=coefficient for the spectral signal component associated with background spectrum.

BKGD=the spectral signal for background spectrum.

$C_1$=concentration coefficient for a first spectral signal component, such as an $F_1$ reporter "pure dye" or first pure component.

$C_2$=concentration coefficient for a second spectral signal component, such as an $F_2$ reporter "pure dye" or second pure component.

$C_3$=concentration coefficient for a third spectral signal component, such as Q quencher "pure dye" or third pure component.

$C_n$=concentration coefficient for an $n^{th}$ spectral signal component for the $F_n$ reporter "pure dye" or $n^{th}$ pure component.

$F_1$=the spectral signal for a first $F_1$ reporter "pure dye" or a first pure component spectrum.

$F_2$=the spectral signal for a second $F_2$ reporter "pure dye" or a second pure component spectrum.

Q=the spectral signal for a Q quencher "pure dye" or a third pure component spectrum.

$F_n$=the spectral signal for an $n^{th}$ $F_n$ reporter "pure dye" or $n^{th}$ pure component.

e=the residual spectral error associated with the spectral model in Equation (1).

Figure 2:
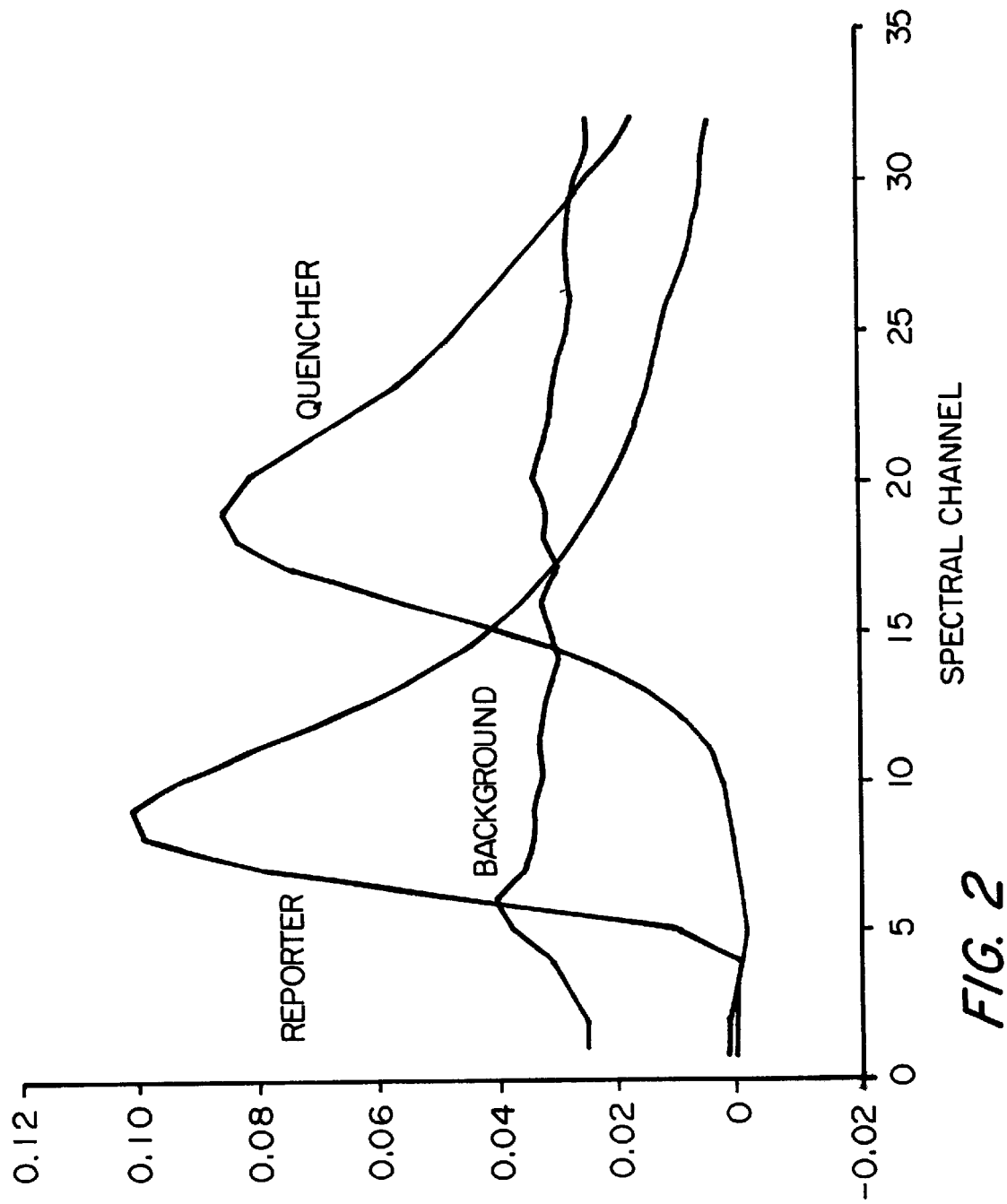
FIG. 2 shows the fluorescence spectra of a reporter, a quencher, and background.

FIG. 2 shows the fluorescence of a reporter, a quencher, and background components for a spectral channel for the spectra of FIG. 1 where the x-axis measures a spectral channel (correlated to wavelength) and the y-axis measures the intensity of fluorescence.

Figure 3:
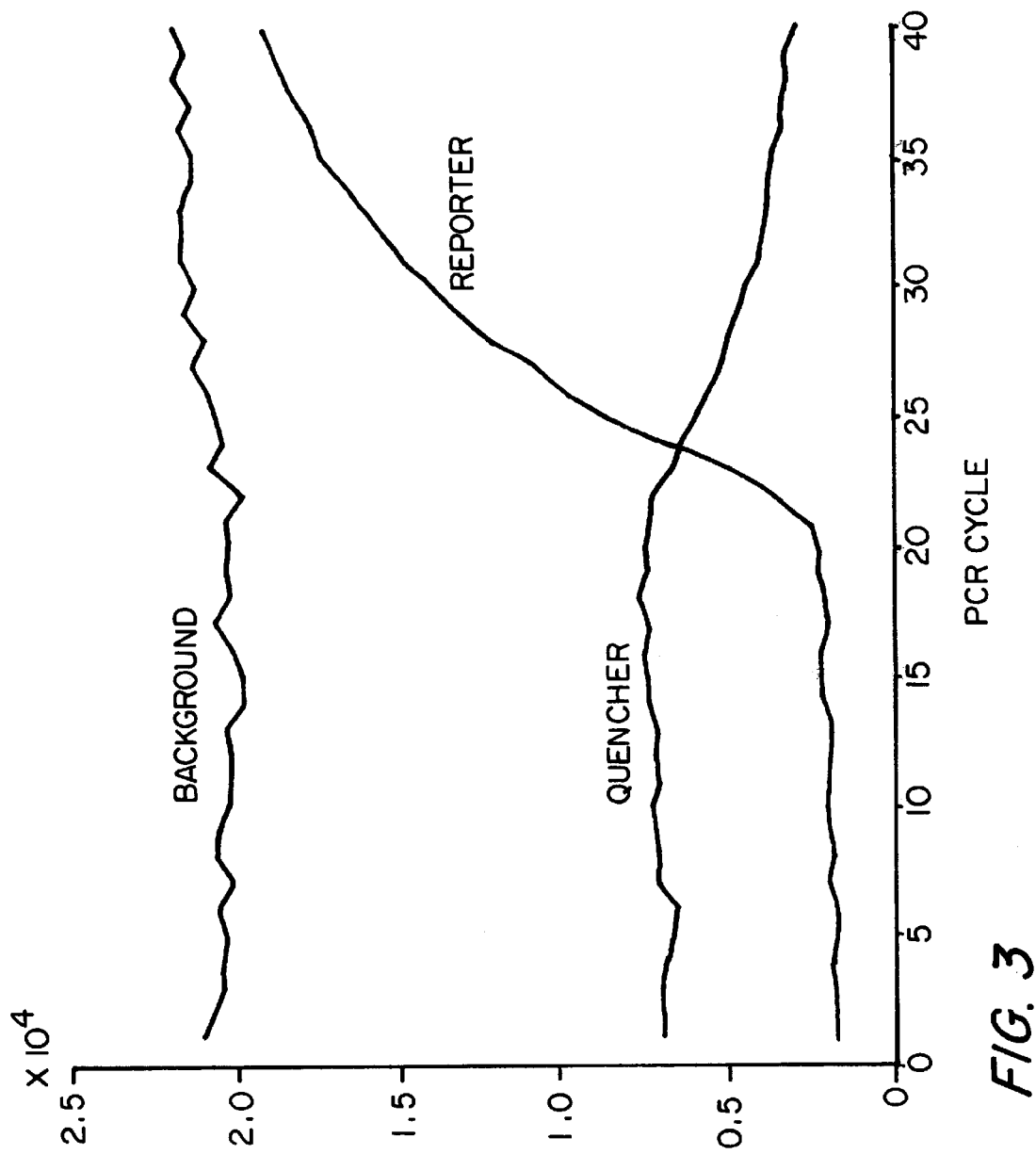
FIG. 3 shows the fluorescence of a reporter, a quencher, and background components associated with each PCR growth cycle.

In the case of PCR amplification, a probe is digested by the nuclease activity of a polymerase when hybridized to a target sequence to cause a fluorescent reporter molecule such as $F_1$ and/or $F_2$ to be separated from a quencher molecule Q, thereby causing fluorescence from the reporter molecules to appear increased as shown FIG. 3.

Figure 4:
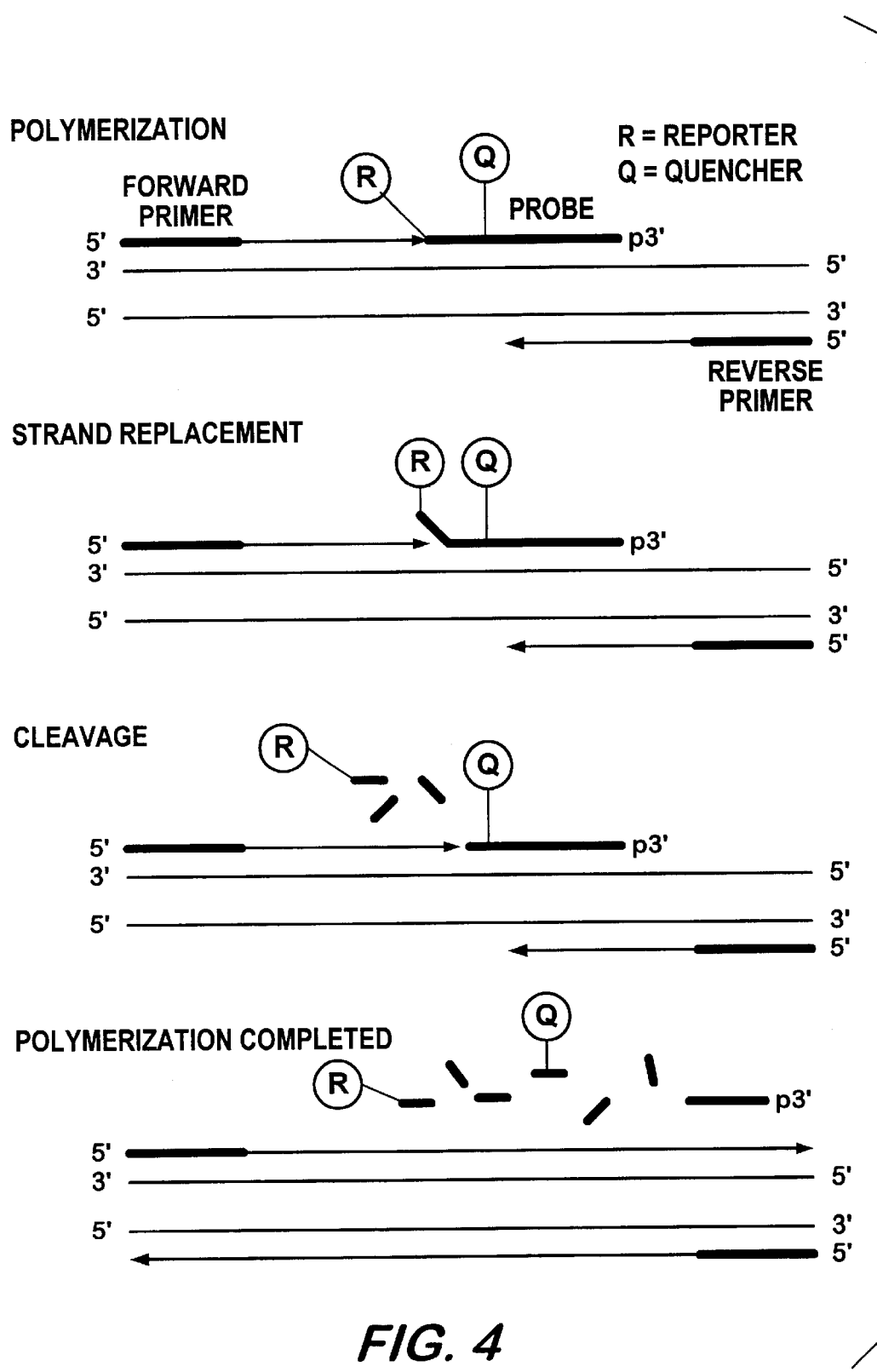
FIG. 4 illustrates a method for real-time monitoring nucleic acid amplification utilizing a probe which is degraded by the 5'→3' exonuclease activity of a nucleic acid polymerase.

The Taq-Man approach, illustrated in FIG. 4, uses an oligonucleotide probe containing a reporter molecule—quencher molecule pair that specifically anneals to a region of a target polynucleotide "downstream", i.e. in the direction of extension of primer binding sites. The reporter molecule and quencher molecule are positioned on the probe sufficiently close to each other such that whenever the reporter molecule is excited, the energy of the excited state nonradiatively transfers to the quencher molecule where it either dissipates nonradiatively or is emitted at a different emission frequency than that of the reporter molecule. During strand extension by a DNA polymerase, the probe anneals to the template where it is digested by the 5'→3' exonuclease activity of the polymerase. As a result of the probe being digested, the reporter molecule is effectively separated from the quencher molecule such that the quencher molecule is no longer close enough to the reporter molecule to quench the reporter molecule's fluorescence. Thus, as more and more probes are digested during amplification, the number of reporter molecules in solution increases, thus resulting in an increasing number of unquenched reporter molecules which produce a stronger and stronger fluorescent signal.

FIG. 5 is a logic flow diagram using the iterative spectral compensation method of the present invention, shown as computer software 20 linked to an analytical apparatus or device such as a spectrophotometer 10 and monitor 40.

The first aspect of the method of the present invention corrects for spectral cross-talk in the raw signal represented by equation (1), by obtaining 21 a first set of data corresponding to a spectrum of the sample, retrieving 22 a second set of data corresponding to spectra for at least one pure component of spectrum, and resolving 26 the signal data into respective contributions associated with pure component signals and a residual e. This can be represented in matrix form as;

$$Y = [C_o, C_1, C_2, C_3, \ldots, Cn] \cdot \begin{bmatrix} BKGD \\ F_1 \\ F_2 \\ Q \\ \vdots \\ Fn \end{bmatrix} + e \quad (2)$$

and reduced to;

$$Y = C \cdot K \quad (3)$$

where, $$C = [C_o, C_1, C_2, C_3, \ldots, C_n] \text{ and } K = \begin{bmatrix} BKGD \\ F_1 \\ F_2 \\ Q \\ \vdots \\ F_n \end{bmatrix}$$

where C is a 1×(n+1) matrix representing data corresponding to the concentration (or signal) coefficients for the pure or separate components. and K is a (n+1)×p matrix representing data corresponding to the spectra for the pure or separate components at p different spectral channels.

Matrix C represents an estimate of the concentration of each individual spectrally resolvable species in a mixture based on a spectral response which includes contributions from the background and all multiple spatially overlapping species (i.e., n+1 of them).

Matrix K represents the individual contribution of the spectral signal components for each of the pure species measured at p different fluorescence emission wavelengths. Such a second set of data, as represented by Matrix K, corresponding to spectra for the pure components of the spectrum sample can be stored and later retrieved in a software application. Matrix C can be derived from Y (dimensioned (1×p) to contain total fluorescence emissions at p different wavelengths) by $$C = Y \cdot K^+ \quad (4)$$

or $$C = Y \cdot K^T (KK^T)^{-1} \quad (5)$$

where the superscript T indicates the transpose operation and the superscript −1 or + indicates the matrix inversion.

The concentration matrix C is estimated by arriving at the best linear combination of pure component signals to fit the measured raw spectra, such as by example, and not as a limitation to the present invention, a multi component model according to Equation (1). See also PCT International Publication WO 97/146963 to Sharaf, incorporated herein by reference.

The second aspect of the method of the present invention compensates or corrects for spectral shift. In the case of a first reporter dye $F_1$ or first pure component, a first derivative of the curve associated with the spectral response of pure reporter dye component, F1 is calculated 24, using by way of example and not as a limitation to the present invention, the Savitzky-Golay method. See A. Savitzky; E. Golay, *Smoothing And Differentiation Of Data By Simplified Least Squares Procedures,* Anal. Chem. 1964, pp. 1627–1639. The following equation is then employed to estimate the degree of spectral shift $\Delta\lambda$ for this pure component;

$$[F_1]_t = [F_1]_o + \frac{d[F_1]_o}{d\lambda} \cdot \Delta\lambda_1 \quad (6)$$

where $$\frac{d[F_1]_o}{d\lambda} = \text{a first derivative of the first pure component spectrum } F_l$$

$[F_1]_o$ = a first pure component spectrum
$[F_1]_t$ = a first pure component spectrum corrected for spectral shift $\Delta\lambda_1$.

Each first derivative is calculated for each of the other pure dye or pure component spectra such as $F_2$, Q, . . . , Fn, as outlined above.

After the pure component derivatives are calculated, the raw spectral data signal is fit to account for spectral shifts according to the following operation;

$$Y = C' \cdot K' + e \quad (7)$$

where;

$$C' = [C_o, C_1, C'_1, C_2, C'_2, C_{3'}, C'_3, \ldots, C_n, C'_n]$$

$$K' = \begin{bmatrix} BKGD \\ F_1 \\ F'_1 \\ F_2 \\ F'_2 \\ Q \\ Q' \\ \vdots \\ F_n \\ F'_n \end{bmatrix}$$

and where;
$C_1' = C_1 \Delta\lambda_1$
$C_2' = C_2 \Delta\lambda_2$
$C_3' = C_3 \Delta\lambda_3$ .
.
.
$C_n' = C_n \Delta\lambda_n$
$F_1'$ = first derivative of the $F_1$ pure dye signal
$F_2'$ = first derivative of the $F_2$ pure dye signal
$Q'$ = first derivative of the Q pure dye signal
$Fn'$ = first derivative of the Fn pure dye signal As described in the first step, the concentration matrix C' is derived by the operations represented in equation (5). The pure signal components are observed to be shifted by an amount determined by their respective first derivative components, $F_1'$, $F_2'$, $Q'$, . . . , Fn', and a multicomponent model as outlined in equation 1 is then pre-adjusted for this spectral shift by inclusion of the first derivative terms in the equation, and as represented by the matrix operation of equation (7). The first derivative for background is not included due to its broad spectral feature.

At this point the third aspect of the method of the invention is applied, namely the iterative process to minimize error propagation. The iterative process involves i) selecting a pre-shifted value for $\Delta\lambda(k)$ as shown in equation (8) to compensate for spectral shift;

$$\Delta\lambda i(k) = \frac{Ci'(k)}{Ci(k)} \quad (8)$$

where $Ci'^{(k)}$ and $Ci^{(k)}$ are the coefficients estimated from Eqn. (7) during the iteration. ii) adjusting the "pure" spectral components, such as "pure dye" components $F_1$, $F_2$, Q, up to Fn for their shifts through interpolation such as cubic spline and iii) re-computing the first derivative pure components $F_1'$, $F_2'$, Q' Fn' using, as an example and not as a limitation to the present invention, the Savitzky-Golay method. The cubic spline interpolation may be done as outlined in; C. de Boor, *A Practical Guide to Splines,* Applied Math. Sciences Vol 27, Springer Verlag, New York, 1978, incorporated herein by reference.

An accumulated shift (shown as step 28 in FIG. 5) can be calculated as;

$$\Delta\lambda i = \sum_{j=1}^{k} \Delta\lambda_i(j) \quad (9)$$

where k=the iteration number

In successive iterations, pre-shifting (shown as step 31 in FIG. 5) is best accomplished by interpolation with accumulated shift $\Delta\lambda i$ on the original pure components spectra rather than with incremental shift $\Delta\lambda i^{(k)}$ on previously interpolated data. This way the error propagation through multiple interpolation can be minimized.

It is known that some of the components are not subject to shift or are subject to the same shift, and in this case the corresponding derivatives can be either dropped or constrained to be the same shift. A straight least squares fit can be used or a constrained multiple least squares can be used for estimation of coefficients with higher precision.

The iterative process is run for a sufficient number of times such that the amount of shift at $k^{th}$ iteration is below a user-defined and/or pre-determined error term value $\epsilon$, (i.e., $1 \times 10^{-4}$ or 0.01% of the wavelength interval) shown as step 30 in FIG. 5. This can be represented as;

$$\Delta\lambda i(k) < \epsilon = 1 \times 10^{-4} \quad (10)$$

for any i=1, 2, . . . , n.

In applications for certain spectral data generated with PCR analysis, the above iteration may converge within $\epsilon$ in about three runs.

Once the iteration is complete, the multicomponent model according to equation (1) is applied using the corrected pure components, such as $F_1$, $F_2$, and Q, up to $F_n$ calculated from step ii) of the iteration process outlined above according to the accumulated shift $\Delta\lambda i$ in Equation (9) (shown as step 32 in FIG. 5). The final pure components contribution C to the raw signal can then be calculated as outlined in equations (3), (4), and (5) without the inclusion of all derivative terms (shown as steps 32 and 34 in FIG. 5) to eliminate excessive noise amplification through first derivative terms.

The above method allows for quantification of pure components in a multicomponent mix, such as for example, and not as a limitation to the present invention, determination of the presence and amount of fluorescent markers such as reporters and quenchers in DNA PCR analysis. One of the advantages of the present invention is improved accuracy and precision for determination of spectrally overlapping pure components in a multicomponent system from the spectral raw data generated. This is accomplished by the method of the present invention which employs a pre-shifting of spectral data associated with the presence of pure components in the calculation and application of derivative data to account for such spectral shift. As result, the iteration may converge in as little as three runs, and reduces propagation of error associated with the least squares fit. This is achieved because the iteration allows for a correction in the pure component spectra and applies only the corrected pure component spectra in a final calculation to obtain the pure component concentration coefficients of a multicomponent system. This provides good accuracy because the derivative term of the pure component spectral signals are statistically insignificant once a reasonable convergence has occurred, i.e., $\epsilon \leq 1 \times 10^{-4}$. Consequently, when applying a multicomponent model to fit the raw spectral data, the error propagation associated with a greater number of components in a multicomponent system is reduced. This occurs because the derivative terms used to correct for the spectral shift are not needed in the final calculation to obtain the concentration coefficients of the pure components. Therefore the method provides a more accurate determination using spectral data that accounts for spectral shift, while at the same time reduces the propagation of error associated with past methods to correct for such shift, and does so with few computational steps resulting in a relatively fast convergence i.e., in about three runs.

It is understood that the method of the present invention is not specifically limited to correction for spectral shift or overlap in a PCR application or an application using fluorescent markers, but could be applied to any analytical method that seeks to resolve a signal into pure component(s) from analysis of a sample. As an example and not as a limitation to the present invention, the method could be applied to 1) atomic absorption spectroscopy, 2) atomic emission spectroscopy, 3) UV-Vis or IR spectrometry, 4) electrophoresis, 5) chromatography, 6) mass spectrometry, 7) spectral imaging and other separation or detection techniques where a multicomponent mixture can be resolved into pure components.

As mentioned, the method of the present invention is not specifically limited to application with fluorescence spectroscopy but could be applied to any analytical detection technique where a sample's components are determined by a characteristic measurement associated with at least two variables, as an example, and not as a limitation of the present invention, the method could be applied to FTIR spectroscopy, mass spectrometry, electrochemical detection, NMR, photoacoustic detection, circular dichroism, chromatography, atomic spectroscopy, and other analytical techniques.

The above description is intended to enable the person skilled in the art to practice the invention. It is not intended to detail all possible modifications and variations which will become apparent to one skilled worker upon reading the description. It is intended, however, that all such modifications and variations be included within the scope of the invention which is defined by the following claims. The claims are meant to cover the indicated elements and steps in any arrangement or sequence which is effective to meet the objectives intended for the invention, unless the context specifically indicates the contrary.

What is claimed is:

1. A method for compensating for spectral shift in the spectrometric analysis of a sample comprising the steps of:

obtaining a first set of data corresponding to a spectrum of the sample;

retrieving a second set of data corresponding to spectra for at least one pure component of said spectrum;

calculating a first derivative for said second set of data;

resolving said first set of data into said second set of data, said first derivative, and at least one concentration coefficient for said pure component;

pre-shifting said second set of data to compensate for the spectral shift;

further calculating a residual error associated with the spectral shift for said first set of data; and repeating said pre-shifting and further calculating steps until said residual error is within a pre-determined value.

2. The method of claim 1 further comprising the step of further resolving said first set of data into said second set of data and at least one concentration coefficient for said pure component without use of said first derivative.

3. The method of claim 2 wherein said further resolving step includes adjusting said concentration coefficient to account for the spectral shift compensated for as a result of performing any one of said pre-shifting, further calculating, and repeating steps.

4. The method of claim 2 wherein said second set of data corresponds to spectra for more than one pure component of said spectrum; and said resolving step resolves said first set of data into more than one concentration coefficient for said pure components.

5. The method of claim 4 wherein said first set of data comprises the matrix represented by C and said second set of data further comprises the matrix represented by K.

6. The method of claim 5 wherein said K matrix comprises data corresponding to at least one reporter pure dye and at least one quencher pure dye in a PCR analysis.

7. The method of claim 5 wherein said adjusting of said concentration coefficient further comprises constructing a matrix model for a multicomponent sample according to the equation;

$$Y = C \cdot K.$$

8. The method of claim 7 wherein said pre-shifting step includes compensating for spectral shift according to the equation;

$$\Delta \lambda i(k) = \frac{Ci'(k)}{Ci(k)}.$$

9. The method of claim 8 wherein said repeating step includes calculating an accumulated shift according to the equation;

$$\Delta\lambda i = \sum_{j=1}^{k} \Delta\lambda_i(j).$$

10. A method for resolving a signal into at least one separate component and compensating for a signal shift in the analysis of a sample comprising steps of:
   resolving the signal into a first set of data of at least one separate component and a second set of data of at least one coefficient for said separate component;
   retrieving said first set of data corresponding to said component of the sample;
   calculating a first derivative for said first set of data;
   second resolving the signal into said first set of data, said second set of data, and said first derivative;
   pre-shifting said first set of data to compensate for the signal shift;
   further calculating a residual error associated with the signal shift for the signal; and
   comparing said residual error with a pre-determined value; and
   repeating said pre-shifting, further calculating and comparing steps until said residual error is within said pre-determined value.

11. The method of claim 10 further comprising the step of:
   further resolving said first set of data into said second set of data and a coefficient for said pure component without use of said first derivative.

12. The method of claim 11 wherein said first set of data contains more than one component and said second set of data contains more than one coefficient for said components.

13. The method of claim 11 wherein said further resolving step includes adjusting said coefficient to account for the signal shift compensated for as a result of performing any one of said pre-shifting, further calculating, and repeating steps.

14. The method of claim 13 wherein said pre-shifting step includes compensating for spectral shift according to the equation;

$$\Delta\lambda i(k) = \frac{Ci'(k)}{Ci(k)}.$$

15. The method of claim 14 wherein said repeating step includes calculating an accumulated shift according to the equation;

$$\Delta\lambda i = \sum_{j=1}^{k} \Delta\lambda_i(j).$$

16. An apparatus for compensating for spectral shift in the spectrometric analysis of a sample comprising:
   a device for obtaining a spectrum of the sample;
   a computer linked to said device;
   software executing on said computer for obtaining a first set of data corresponding to said spectrum of the sample;
   software executing on said computer for retrieving a second set of data corresponding to spectra for at least one pure component of said spectrum;
   software executing on said computer for calculating a first derivative for said second set of data;
   software executing on said computer for resolving said first set of data into said second set of data, said first derivative, and at least one concentration coefficient for said pure component;
   software executing on said computer for pre-shifting said second set of data to compensate for the spectral shift;
   software executing on said computer for further calculating a residual error associated with the spectral shift for said first set of data;
   software executing on said computer for comparing said residual error with a pre-determined value; and
   software executing on said computer for repeating said pre-shifting, further calculating and comparing steps until said residual error is within said pre-determined value.

17. The apparatus of claim 16 wherein said software executing on said computer further resolves said first set of data into said second set of data and at least one concentration coefficient for said pure component without use of said first derivative.

18. The apparatus of claim 17 wherein said software executing on said computer includes adjusting said concentration coefficient to account for the spectral shift compensated for as a result of performing any one of said pre-shifting, further calculating, and repeating steps.

19. The apparatus of claim 17 wherein said software executing on said computer includes said second set of data that corresponds to spectra for more than one pure component of said spectrum; and resolves said first set of data into more than one concentration coefficient for said pure components.

20. The apparatus of claim 19 wherein said software executing on said computer includes said first set of data further comprising the matrix represented by C and said second set of data further comprises the matrix represented by K.

21. The apparatus of claim 20 wherein said K matrix of said software executing on said computer comprises data corresponding to at least one reporter pure dye and at least one quencher pure dye in a PCR analysis.

22. The apparatus of claim 18 wherein said adjusting of said concentration coefficient of said software executing on said computer further comprises constructing a matrix model for a multicomponent sample according to the equation;

$$Y = C \cdot K.$$

23. The apparatus of claim 18 wherein said pre-shifting step of said software executing on said computer includes compensating for spectral shift according to the equation;

$$\Delta\lambda i(k) = \frac{Ci'(k)}{Ci(k)}.$$

24. The apparatus of claim 23 wherein said repeating step of said software executing on said computer includes calculating an accumulated shift according to the equation;

$$\Delta\lambda i = \sum_{j=1}^{k} \Delta\lambda_i(j).$$

* * * * *